US009931232B2

(12) United States Patent
Gunderson et al.

(10) Patent No.: US 9,931,232 B2
(45) Date of Patent: Apr. 3, 2018

(54) STENT DELIVERY SYSTEM

(75) Inventors: Richard Charles Gunderson, Maple Grove, MN (US); Katherine M. Prindle, Robbinsdale, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 211 days.

(21) Appl. No.: 13/243,146

(22) Filed: Sep. 23, 2011

(65) Prior Publication Data

US 2012/0101562 A1    Apr. 26, 2012

Related U.S. Application Data

(60) Provisional application No. 61/405,575, filed on Oct. 21, 2010.

(51) Int. Cl.
A61F 2/06    (2013.01)
A61F 2/966   (2013.01)
A61F 2/95    (2013.01)

(52) U.S. Cl.
CPC ............... *A61F 2/966* (2013.01); *A61F 2/95* (2013.01)

(58) Field of Classification Search
CPC .................................. A61F 2/958; A61F 2/95
USPC ................. 623/1.11, 1.12; 606/108
See application file for complete search history.

(56) References Cited

U.S. PATENT DOCUMENTS

| 4,634,432 | A | * | 1/1987 | Kocak | A61M 25/005 |
| | | | | | 137/846 |
| 4,732,152 | A | | 3/1988 | Wallsten et al. | |
| 4,793,348 | A | | 12/1988 | Palmaz | |
| 4,848,343 | A | | 7/1989 | Wallsten et al. | |
| 4,875,480 | A | | 10/1989 | Imbert | |
| 5,071,407 | A | | 12/1991 | Termin et al. | |
| 5,074,845 | A | | 12/1991 | Miraki et al. | |
| 5,158,548 | A | | 10/1992 | Lau et al. | |
| 5,178,618 | A | | 1/1993 | Kandarpa | |
| 5,201,757 | A | | 4/1993 | Heyn et al. | |
| 5,221,261 | A | | 6/1993 | Termin et al. | |
| 5,238,004 | A | | 8/1993 | Sahatjian et al. | |
| 5,344,426 | A | | 9/1994 | Lau et al. | |
| 5,378,239 | A | | 1/1995 | Termin et al. | |
| 5,445,646 | A | | 8/1995 | Euteneuer et al. | |
| 5,496,277 | A | | 3/1996 | Termin et al. | |
| 5,500,181 | A | | 3/1996 | Wang et al. | |
| 5,509,900 | A | | 4/1996 | Kirkman | |

(Continued)

FOREIGN PATENT DOCUMENTS

DE    4242291 A1    6/1994
EP    0278333 A2    8/1988

(Continued)

*Primary Examiner* — Richard Louis

(74) *Attorney, Agent, or Firm* — Seager, Tufte & Wickhem LLP.

(57) ABSTRACT

Stent delivery systems and methods for making and using stent delivery systems are disclosed. An example stent delivery system may include an inner member. A sheath may be disposed about the inner member. The sheath may include a compressible coil. A stent may be disposed between the inner member and the sheath. A membrane may extend between the inner member and the sheath. The membrane may be configured to be disposed on the stent. An outer member may be disposed over the sheath.

10 Claims, 9 Drawing Sheets

(56) References Cited

U.S. PATENT DOCUMENTS

| | | | |
|---|---|---|---|
| 5,534,007 A * | 7/1996 | St. Germain | A61F 2/95 606/191 |
| 5,571,135 A | 11/1996 | Fraser et al. | |
| 5,593,418 A | 1/1997 | Mollenauer | |
| 5,639,274 A | 6/1997 | Fischell et al. | |
| 5,662,703 A | 9/1997 | Yurek et al. | |
| 5,681,345 A | 10/1997 | Euteneuer | |
| 5,690,644 A | 11/1997 | Yurek et al. | |
| 5,702,364 A | 12/1997 | Euteneuer et al. | |
| 5,769,821 A | 6/1998 | Abrahamson et al. | |
| 5,772,609 A | 6/1998 | Nguyen et al. | |
| 5,788,707 A | 8/1998 | Del Toro et al. | |
| 5,800,517 A | 9/1998 | Anderson et al. | |
| 5,833,657 A | 11/1998 | Reinhardt et al. | |
| 5,935,135 A | 8/1999 | Bramfitt et al. | |
| 6,019,779 A * | 2/2000 | Thorud | A61F 2/88 606/198 |
| 6,059,813 A | 5/2000 | Vrba et al. | |
| 6,066,155 A | 5/2000 | Amann et al. | |
| 6,071,263 A | 6/2000 | Kirkman | |
| 6,083,257 A | 7/2000 | Taylor et al. | |
| 6,096,045 A | 8/2000 | Del Toro et al. | |
| 6,123,720 A | 9/2000 | Anderson et al. | |
| 6,139,510 A | 10/2000 | Palell | |
| 6,183,508 B1 | 2/2001 | Stinson et al. | |
| 6,221,097 B1 | 4/2001 | Wang et al. | |
| 6,238,410 B1 | 5/2001 | Vrba et al. | |
| 6,280,412 B1 | 8/2001 | Pederson et al. | |
| 6,331,186 B1 | 12/2001 | Wang et al. | |
| 6,342,066 B1 | 1/2002 | Toro et al. | |
| 6,350,277 B1 | 2/2002 | Kocur | |
| 6,443,880 B2 | 9/2002 | Blais et al. | |
| 6,464,718 B1 | 10/2002 | Miller et al. | |
| 6,478,814 B2 | 11/2002 | Wang et al. | |
| 6,508,803 B1 | 1/2003 | Horikawa et al. | |
| 6,544,278 B1 | 4/2003 | Vrba et al. | |
| 6,702,802 B1 * | 3/2004 | Hancock | A61F 2/958 604/104 |
| 6,755,855 B2 | 6/2004 | Yurek et al. | |
| 6,942,682 B2 | 9/2005 | Vrba et al. | |
| 7,393,358 B2 | 7/2008 | Malewicz | |
| 2002/0072729 A1 * | 6/2002 | Hoste | A61M 25/005 604/524 |
| 2003/0004537 A1 * | 1/2003 | Boyle et al. | 606/200 |
| 2003/0009184 A1 * | 1/2003 | Pepin | A61M 25/005 606/159 |
| 2003/0176910 A1 | 9/2003 | Vrba et al. | |
| 2004/0143272 A1 | 7/2004 | Cully et al. | |
| 2004/0143315 A1 | 7/2004 | Bruun et al. | |
| 2004/0167603 A1 | 8/2004 | Jackson et al. | |
| 2004/0199175 A1 * | 10/2004 | Jaeger et al. | 606/108 |
| 2004/0199239 A1 | 10/2004 | Austin et al. | |
| 2005/0033402 A1 | 2/2005 | Cully et al. | |
| 2005/0038495 A1 | 2/2005 | Greenan | |
| 2006/0030923 A1 | 2/2006 | Gunderson | |
| 2006/0161197 A1 * | 7/2006 | Paul et al. | 606/195 |
| 2006/0282112 A1 * | 12/2006 | Griffin | A61B 17/12022 606/200 |
| 2007/0208350 A1 * | 9/2007 | Gunderson | A61F 2/95 606/108 |
| 2008/0065013 A1 * | 3/2008 | Goodin | A61M 25/0052 604/103.09 |
| 2009/0259298 A1 * | 10/2009 | Mayberry et al. | 623/1.35 |
| 2009/0319019 A1 * | 12/2009 | Parker | A61F 2/95 623/1.11 |

FOREIGN PATENT DOCUMENTS

| | | |
|---|---|---|
| EP | 0537985 A2 | 4/1993 |
| EP | 0684022 A2 | 11/1995 |
| WO | WO 92/12681 A1 | 8/1992 |
| WO | WO 93/17747 A1 | 9/1993 |
| WO | WO 93/19703 A1 | 10/1993 |
| WO | WO 94/15549 A1 | 7/1994 |
| WO | WO 95/10317 A1 | 4/1995 |
| WO | WO 95/23563 A1 | 9/1995 |
| WO | WO 96/32078 A1 | 10/1996 |
| WO | WO 97/16133 A1 | 5/1997 |
| WO | WO 98/07387 A1 | 2/1998 |
| WO | WO 98/52496 A1 | 11/1998 |
| WO | WO 00/27309 A1 | 5/2000 |
| WO | WO 01/78627 A1 | 10/2001 |
| WO | WO 02/38084 A2 | 5/2002 |
| WO | WO 2004/066809 A2 | 8/2004 |
| WO | WO 2010/076052 A1 | 7/2010 |
| WO | WO 2010/120671 A1 | 10/2010 |

* cited by examiner ary of some embodiments is not intended to describe each disclosed embodiment or every implementation of the present invention. The Figures, and Detailed Description, which follow, more particularly exemplify these embodiments.

STENT DELIVERY SYSTEM

CROSS-REFERENCE TO RELATED APPLICATION

This application claims the benefit of U.S. Provisional Application Ser. No. 61/405,575, filed Oct. 21, 2010, the entire disclosure of which is incorporated herein by reference.

TECHNICAL FIELD

The present invention pertains to medical devices and methods for making and using medical devices. More particularly, the present invention pertains to stent delivery systems.

BACKGROUND

A wide variety of intracorporeal medical devices have been developed for medical use, for example, intravascular use. Some of these devices include stent delivery systems. These devices are manufactured by any one of a variety of different manufacturing methods and may be used according to any one of a variety of methods. Of the known stent delivery devices and methods for making and using the same, each has certain advantages and disadvantages. There is an ongoing need to provide alternative stent delivery devices as well as alternative methods for making and using stent delivery devices.

BRIEF SUMMARY

The invention provides design, material, manufacturing method, and use alternatives for stent delivery systems including self-expanding stent delivery systems. An example stent delivery system may include an inner member. A sheath may be disposed about the inner member. The sheath may include a compressible coil. A stent may be disposed between the inner member and the sheath. A membrane may extend between the inner member and the sheath. The membrane may be configured to be disposed on the stent. An outer member may be disposed over the sheath.

An example self-expanding stent delivery system may include an inner member having a guidewire lumen formed therein and may include a distal tip. A sheath may be disposed about the inner member. The sheath may include a compressible coil that is configured to shift between a non-compressed configuration and a compressed configuration. A pull wire may be attached to a distal portion of the sheath and may extend proximally therefrom. Proximal retraction of the pull wire may result in shifting of the compressible coil from the non-compressed configuration to the compressed configuration. A stent may be disposed between the inner member and the sheath. A rolling membrane may extend between the inner member and the sheath. An outer member may be disposed over a proximal portion of the sheath.

An example method for delivering a self-expanding stent may include providing a self-expanding stent delivery system. The self-expanding delivery system may include an inner member having a guidewire lumen formed therein and including a distal tip, a sheath disposed about the inner member that may include a compressible coil that is configured to shift between a non-compressed configuration and a compressed configuration, a pull wire attached to a distal portion of the sheath and extending proximally therefrom and configured such that proximal retraction of the pull wire results in shifting of the compressible coil from the non-compressed configuration to the compressed configuration, a stent disposed between the inner member and the sheath, a rolling membrane extending between the inner member and the sheath, an outer member disposed over a proximal portion of the sheath, and a handle disposed at a proximal end of the self-expanding stent delivery system, the handle including a pressurization port for infusing fluid into a pressurization lumen defined between the inner member and the sheath. The method may also include advancing the self-expanding stent delivery system through the vasculature of a patient to a position adjacent an area of interest, infusing fluid into the pressurization lumen, and proximally retracting the pull wire to shift the compressible coil from the non-compressed configuration to the compressed configuration and to proximally retract the sheath.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
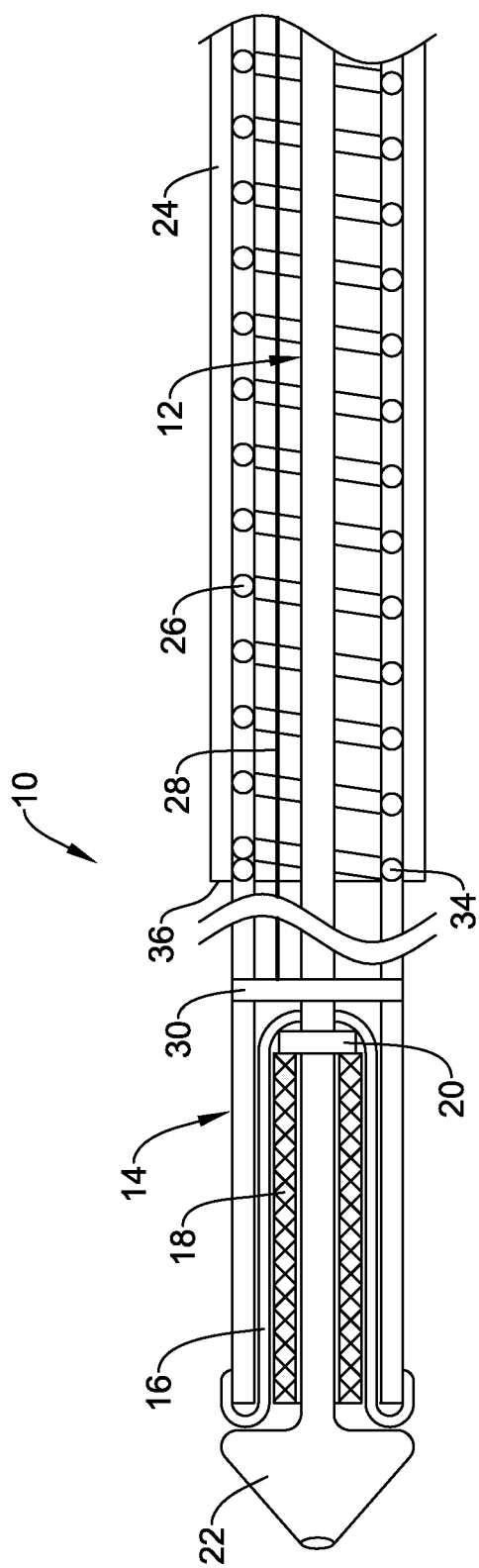
FIG. 1 is a partial cross-sectional side view of an example stent delivery system.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

The ability to accurately deploy a stent within the vasculature may be an important feature considered when designing stent delivery systems. Some self-expanding stent delivery systems utilize a rolling membrane to improve deployment accuracy. In general, a rolling membrane is a structure that covers the stent during delivery and then "rolls" proximally to uncover the stent. The rolling motion of the membrane may help to reduce the likelihood that longitudinal shifting the stent may occur during deployment. Rolling membranes reduce longitudinal displacement of the stent that may occur when an outer sheath is proximally retracted to expose and deploy the stent in the vasculature.

When deploying a stent using a rolling membrane stent delivery system, the pull back member or deployment sheath that is attached to the rolling membrane may need to be proximally retracted a distance equal to about two times the length of the stent. For example, in order to deliver a 200 mm stent, the deployment sheath would need to travel back 200 mm (for it to be proximal of the stent) plus another 200 mm or so in order for the rolling membrane to also be proximally retracted from the stent. The handle or retraction mechanism for use with these types of systems would, thus, need to be sufficiently long in order to be able to cause retraction across such a distance.

It can be appreciated that as the retraction distance increases, it may be more difficult to use or otherwise manage a standard guidewire with these stent delivery systems. For example, if the stent delivery system is a 120 cm useable length system, the guidewire exchange length would be the 120 cm useable length plus the length of the handle. If the handle needs to be able to allow for the pulling back of the deployment sheath on the order of another 400 mm or so, the overall length of the system may be 180 cm or longer. An appropriate guidewire for use with such a system, thus, would need to be longer than 180 cm. As the length of the guidewire increases, it may be more difficult to manage the guidewire and keep it stationary, particularly if the length becomes sufficiently long so that it is no longer practical for a clinician to hold onto the guidewire during an intervention. Furthermore, some clinicians may have a preference for a particular style, brand, or length of guidewire for use in a clinical intervention. It may be desirable to clinicians if a particular stent delivery system could be used that did not require the use of a "specialized" or "extra long" guidewire.

The stent delivery systems disclosed herein are designed to help reduce the overall length of the stent delivery systems. Because of this, shorter guidewires may be used with the systems disclosed herein, which may allow the user to satisfactorily manage and keep stationary the end of the guidewire during performance of an intervention. Furthermore, this may allow a clinician to use their preferred guidewire in conjunction with a number of different stent delivery interventions.

FIG. 1 illustrates an example stent delivery system 10. System 10 may include an inner member 12 and a sheath 14. A guidewire lumen (not shown) may be formed in inner member 12 so that system 10 may be advanced through the vasculature over a guidewire. A rolling membrane 16 may be attached to outer sheath 14 and inner member 12. For example, membrane 16 may attach to the outer surface of inner member 12 and to an outer or end surface (e.g., an abutting or butt-type joint) of sheath 14. A stent 18 may be disposed about inner member 12. In at least some embodiments, stent 18 is a self-expanding stent. Self-expanding stents are configured to shift from a radially compressed state to an expanded or deployed state suitable for expanding an intravascular lesion. A stent bumper 20 may be disposed on inner member 12, for example, adjacent the proximal end of stent 18. Bumper 20 may be formed of or otherwise include a radiopaque material and it may be configured to reduce proximal shifting of stent 18 that might otherwise occur during deployment of stent 18. An atraumatic tip 22 may be attached to or otherwise formed at the distal end of inner member 12. Some of the components of system 10 may be similar to those in U.S. Patent Application Pub. No. US 2006/0030923, the entire disclosure of which is herein incorporated by reference.

An outer member 24 may be disposed on a portion of sheath 14. Outer member 24 may be similar in form and function to similar structures disclosed in U.S. Patent Application Pub. No. US 2007/0208350, the entire disclosure of which is herein incorporated by reference. Outer member 24 may be longitudinally fixed relative to inner member 12 and may further aid in the reduction of friction between sheath 14 and membrane 16. System 10, as well as numerous other contemplated stent delivery systems, may lack outer member 24.

Sheath 14 may generally be formed from a polymer tube and may include a compressible coil 26. Compressible coil 26 may be disposed within or encapsulated with the wall of sheath 14. Alternatively, sheath 14 may be formed from two or more layers and coil 26 may be disposed between layers. In other embodiments, coil 26 may be disposed within a heat shrink tube or otherwise have a heat shrink polymer coating. Numerous other arrangements are contemplated.

In some embodiments, sheath 14 may include a mid-shaft portion or member (not shown) and compressible coil 26 (in combination with a polymer tube or covering) may be attached to the distal end of the mid-shaft portion. In some of these embodiments, the mid-shaft portion may be disposed underneath outer member 24 and compressible coil 26 may be distal to outer member 24. Numerous other arrangements are contemplated.

The form of coil 26 may vary considerably. For example, coil 26 is illustrated as being formed from a wire having a generally circular cross section. This form, however, is not intended to be limiting. For example, in some embodiments coil 26 may be formed from a wire having a non-circular cross sectional shape. This may include a "ribbon coil" or a coil formed from a wire having a generally rectangular shape. Other shapes and forms are contemplated.

Figure 2:
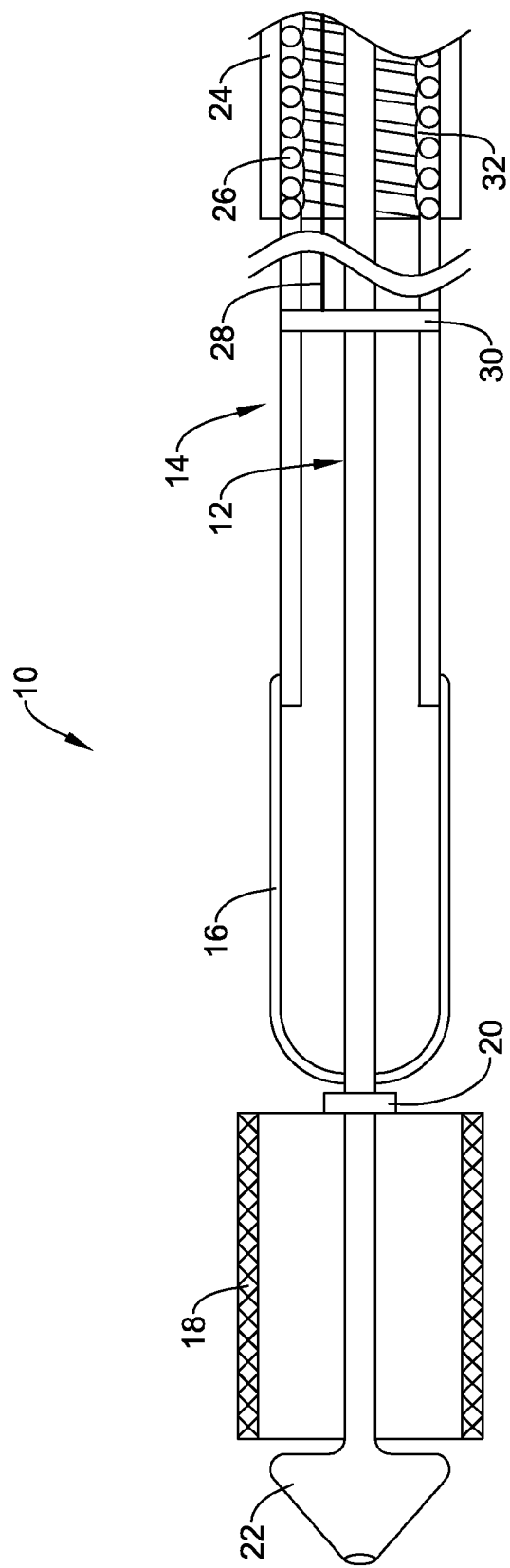
FIG. 2 is a partial cross-sectional side view of the example stent delivery system shown in FIG. 1 with an example compressible coil shown in a compressed configuration.

Compressible coil 26 may add a number of desirable features to sheath 14. For example, coil 26 may add structural support to sheath 14 such that sheath 14 can withstand the infusion of a pressurization fluid therein. In addition, compressible coil 26 may be configured to shift between a first or "non-compressed" configuration (as illustrated in FIG. 1) and a second or "compressed" configuration (as illustrated in FIG. 2). Shifting coil 26 between configurations may occur via a pull wire 28 (e.g., which may take the form of a wire, thread, filament, suture, etc. and may have a substantially round cross section or a non-circular cross section such as rectangular, oval, square, polygonal, etc.) that may be coupled to a distal portion of sheath 14, for example, by a band or collar 30. The exact position of collar 30 may vary. For example, collar 30 may be disposed at the distal end of compressible coil 26. Alternatively, collar 30 may be disposed distally of the distal end of compressible coil 26. In other embodiments, system 10 may lack collar 30 and pull wire 28 may be directly attached to sheath 14 at any suitable location. In still other embodiments, compressible coil 26 may be shifted between configurations using a two or more pull wires 28.

It can be appreciated that when coil 26 is compressed, sheath 14 shortens in length. Because of this, the total distance that sheath 14 needs to be proximally retracted in order to deploy stent 14 is reduced. In addition, when coil 26 is compressed a certain amount of sheath material may be forced outward in order to accommodate the compression of coil 26. In some embodiments, this material may bulge radially outward from the exterior of sheath 14. It may be desirable to limit the amount of material bulging outward so that sheath 14 can remain easily slidable within outer tube 24. This may be accomplished, for example, by reducing the thickness of the polymeric portions of sheath 14 that are adjacent coil 26. In other embodiments, sheath 14 may be configured so that any material that bulges as a result of shifting or compressing coil 26 bulges radially inward. This may be accomplished in a number of different manners. For example, the interior of sheath 14 may be scored, etched, serrated, or otherwise altered so that less resistance to bulging is arranged along the interior of sheath 14. As such, sheath 14 may bulge slightly inward when coil 26 is compressed. Such radially inward bulging is depicted in FIG. 2 and generally bears reference number 32. Other embodiments are also contemplated where sheath 14 bulges both radially inward and outward. Such embodiments may be desirable, for example, because modifications to the inner and outer diameter of sheath 14 can be kept to a minimum.

In general, sheath 14 may be configured so that its outer diameter is altered by less than about 25% as the result of shifting between the non-compressed configuration and the compressed configuration, or less than about 20% as the result of shifting between the non-compressed configuration and the compressed configuration, or less than about 15% as the result of shifting between the non-compressed configuration and the compressed configuration, or less than about 10% as the result of shifting between the non-compressed configuration and the compressed configuration, or less than about 5% as the result of shifting between the non-compressed configuration and the compressed configuration, or less than about 3% as the result of shifting between the non-compressed configuration and the compressed configuration, or less than about 2% as the result of shifting between the non-compressed configuration and the compressed configuration, or less than about 1% as the result of shifting between the non-compressed configuration and the compressed configuration.

The positioning of coil 26 relative to sheath 14 and/or outer tube 24 may also vary. For example, in the embodiment depicted in FIGS. 1-2, the distal end 34 of coil 26 generally aligns with the distal end 36 of outer tube 24. This arrangement may be desirable, for example, because any "bulging" of sheath 14 (as discussed above) may be contained within outer tube 24 and kept from exposure to the vasculature. In other embodiments, however, coil 26 may have a different position.

Figure 3:
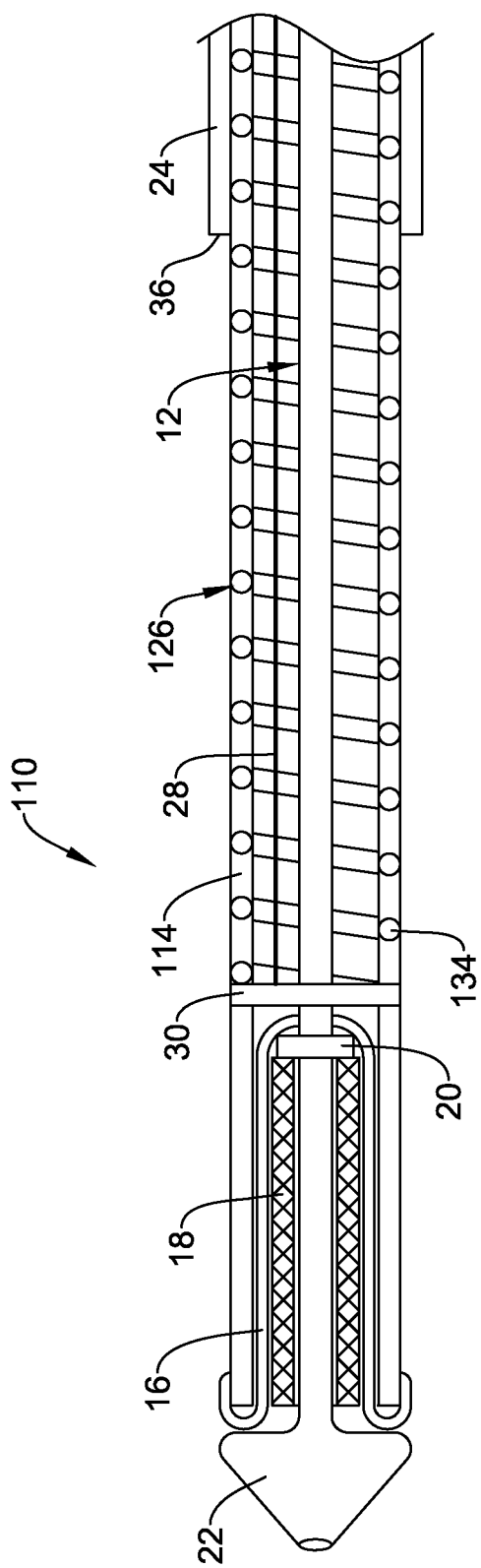
FIG. 3 is a partial cross-sectional side view of another example stent delivery system.
Figure 4:
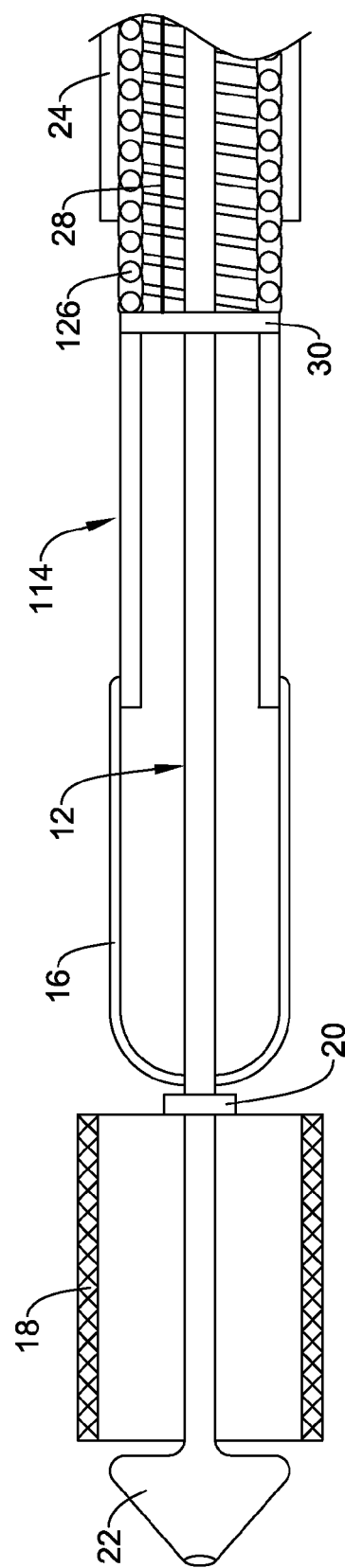
FIG. 4 is a partial cross-sectional side view of the example stent delivery system shown in FIG. 3 with an example compressible coil shown in a compressed configuration.

FIGS. 3-4 illustrate another example stent delivery system 110, which may be similar in form and function to other stent delivery systems disclosed herein, that includes sheath 114 where the distal end 134 of coil 126 extends distally of the distal end 36 of outer tube 24. Just like in system 10, coil 126 can be compressed (for example, as illustrated in FIG. 4) by proximal retraction of pull wire 28.

Figure 5:
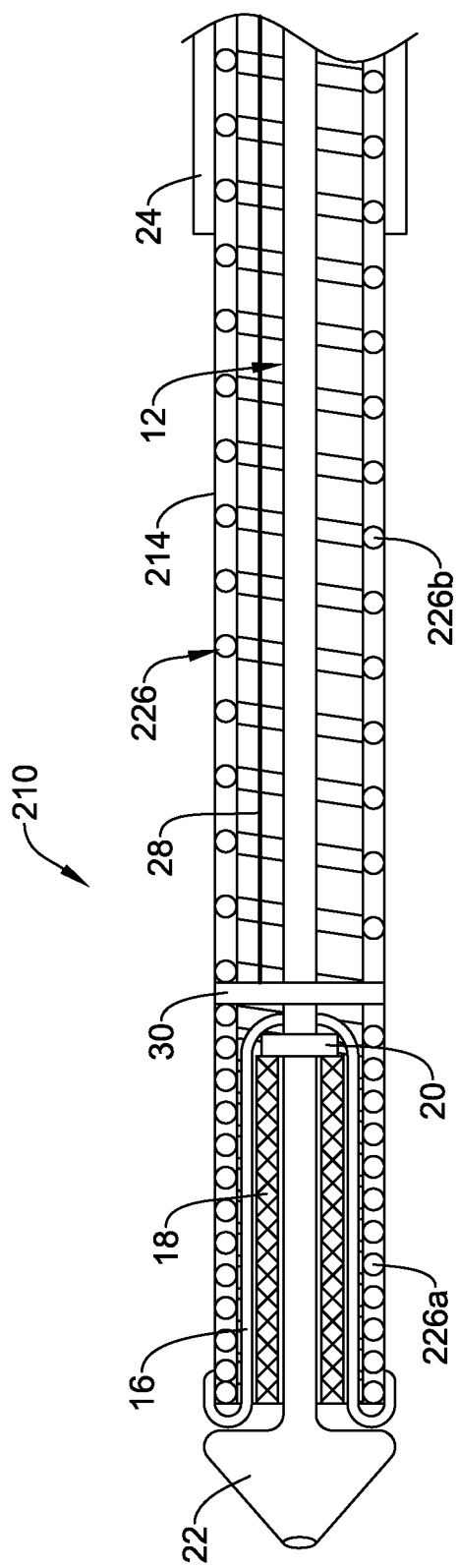
FIG. 5 is a partial cross-sectional side view of another example stent delivery system.
Figure 6:
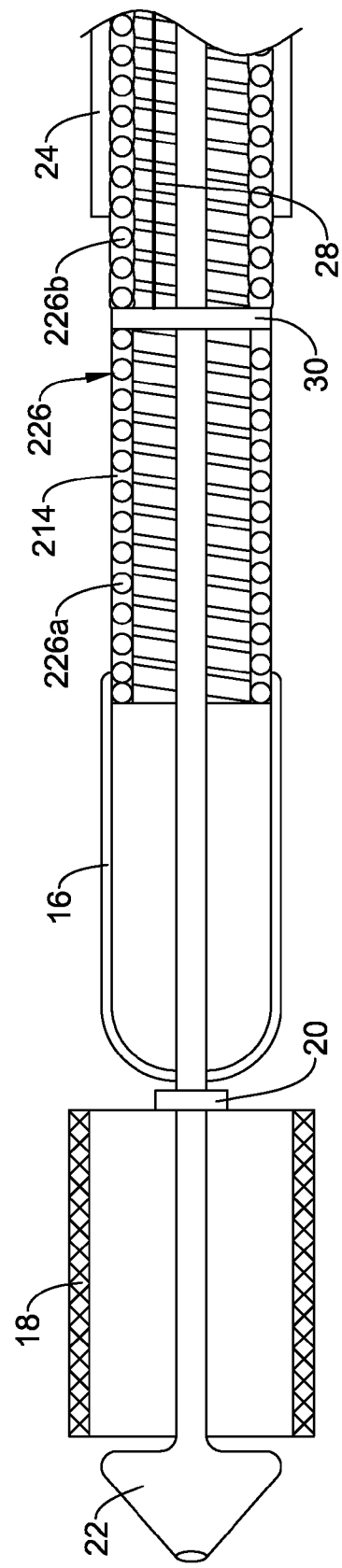
FIG. 6 is a partial cross-sectional side view of the example stent delivery system shown in FIG. 7 with an example compressible coil shown in a compressed configuration.

FIGS. 5-6 illustrate another example stent delivery system 210, which may be similar in form and function to other stent delivery systems disclosed herein, that includes sheath 214 where coil 226 includes a non-compressible portion 226a and a compressible portion 226b. In general, non-compressible portion 226a may have a generally "tight" or "closed" pitch. Such an arrangement may be desirable, for example, because it may provide sheath 214 with increased structural support at this location while still retaining desirable flexibility. Conversely, compressible portion 226b may have a generally "loose" or "open" pitch that can be compressed in a manner similar to how coil 26 is compressed.

The exact location and/or configurations of portions 226a/ 226b may vary. For example, non-compressible portion 226a may generally be disposed adjacent to stent 18 whereas compressible portion 226b may be disposed proximally of non-compressible portion 226a. Other arrangements are contemplated.

Figure 7:
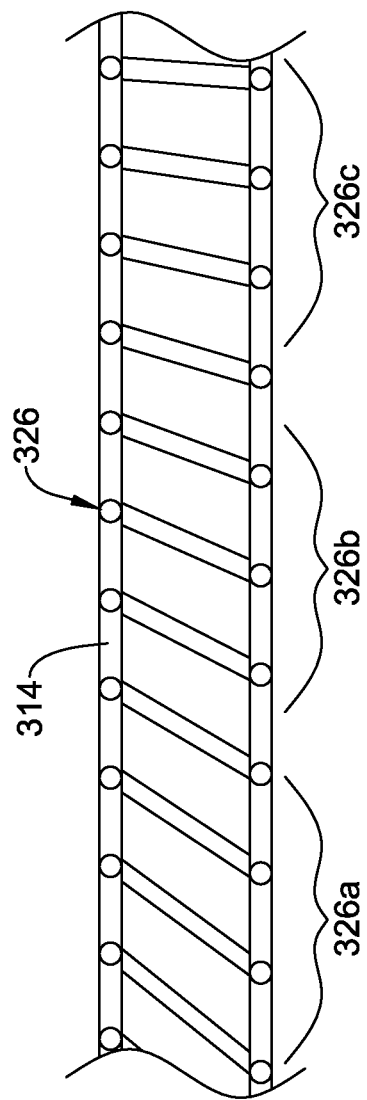
FIG. 7 is a side view of a portion of an example sheath for use with a stent delivery system.

FIG. 7 illustrates another example sheath 314 which may be used with any of the stent delivery systems disclosed herein. Sheath 314 may include compressible coil 326 with a generally variable pitch. A variable pitch may be understood to mean that the angle at which coil 326 winds about sheath 314 changes over a given length. The transition may occur in a step wise manner or gradually over the length of coil 326. For example, coil 326 may have a plurality of sections such as section 326a, 326b, and 326c with a changing pitch. For example, the pitch of coil 326 in section 326a may generally be different from the pitch in section 326b. Likewise, the pitch of coil 326 in section 326b may generally be different from the pitch in section 326c. Within each of sections 326a/326b/326c the pitch may be the same or it may change across the length of the section.

Figure 8:
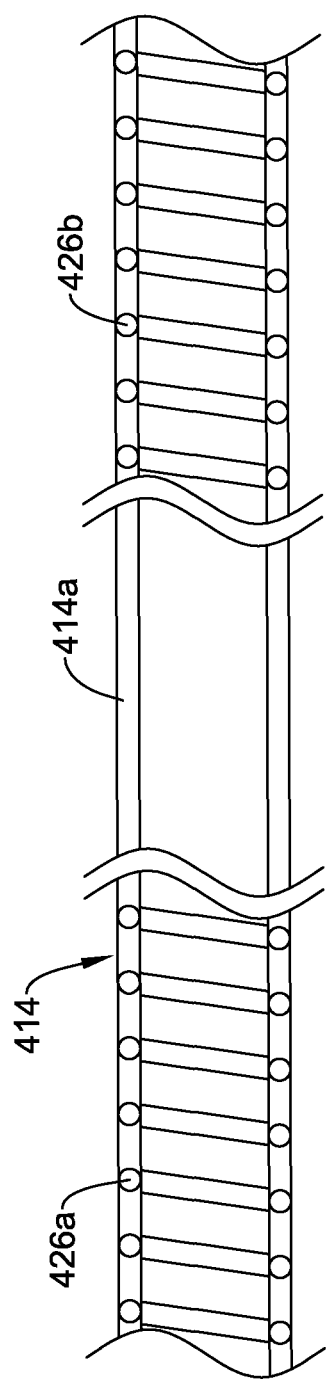
FIG. 8 is a side view of a portion of another example sheath for use with a stent delivery system.

FIG. 8 illustrates another example sheath 414 which may be used with any of the stent delivery systems disclosed herein. In this embodiment, sheath 414 may include a first compressible coil portion 426a and a second compressible coil portion 426b. In some embodiments, sheath 414 may also include additional compressible or non-compressible coil portions. A portion 414a of sheath 414 may lack a compressible coil and generally may be disposed between portions 426a/426b.

In addition to what is disclosed above, numerous other variations are contemplated for the various compressible coils disclosed herein. For example, the size or thickness of the coil may vary, the hardness or spring value may vary, the thickness of a polymer coating disposed thereon, the material of the coil may vary, etc.

Figure 9:
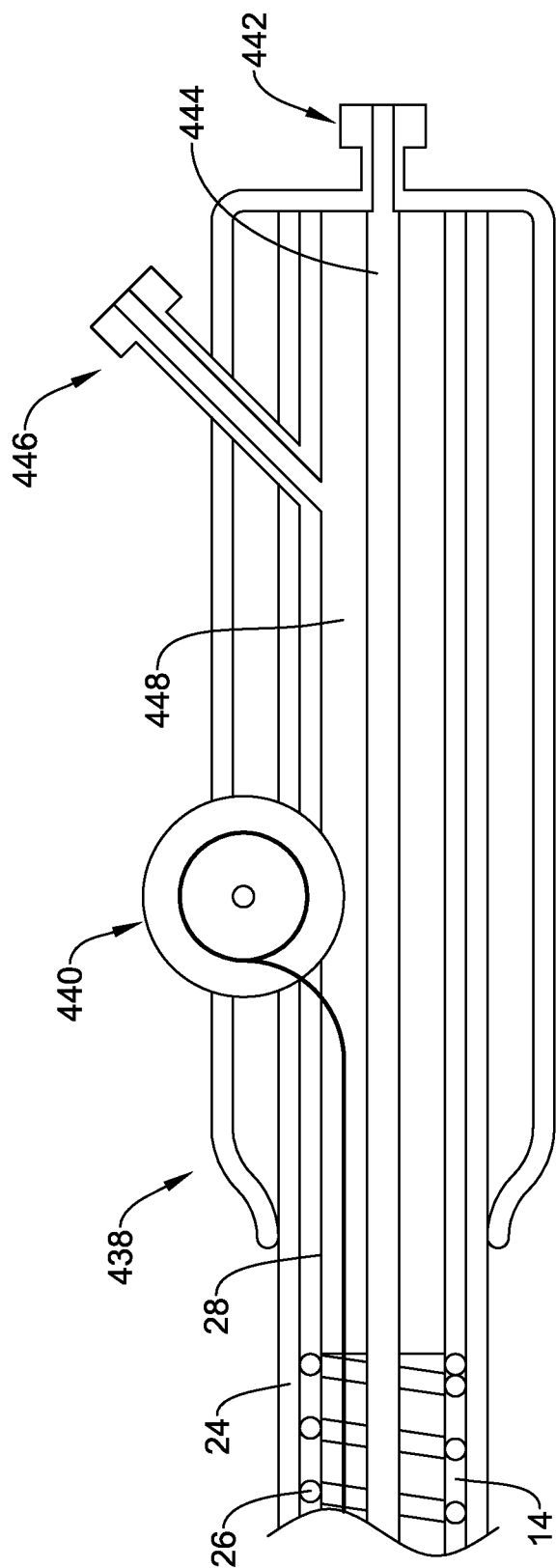
FIG. 9 is a cross-sectional view of a portion of an example handle for use with a stent delivery system.

FIG. 9 generally illustrates a handle 436 for use with any of the stent delivery systems disclosed herein. Handle 436 may include a thumb wheel 440 coupled to pull wire 28. Consequently, rotation of thumb wheel 440 may result in proximal retraction of pull wire 28 and, thus, retraction of sheath 14 and compression of compressible coil 26. Pull wire 28 may be collected on thumb wheel 440 upon rotation thereof or handle 436 may include a secondary or take-up spool (not shown) that may be configured to have pull wire 28 gathered thereon. Handle 436 may also include a guidewire port 442 that provides access to a guidewire lumen 444. Likewise, handle 436 may also include a fluid introduction or pressurization port 446 that provides access to a pressurization lumen 448. Port 446 may allow for pressurization fluid to be infused into lumen 448, which may make it easier to proximally retract sheath 14.

Because handle 436 may include a structure for taking up pull wire 28 (e.g., thumb wheel 440 or a take-up spool) and because this structure may be configured to have a reasonably long length of pull wire 28 gathered thereon, handle 436 may be designed as a "one size fits all" handle when used in combination with stent delivery systems like those disclosed herein. For example, as the length of a particular stent increases, typical handles will also need to increase in size in order to accommodate the proximal shifting of the sheath. However, when used with the stent delivery systems disclosed herein (e.g., which include a compressible coil such as coil 26/126/226/326/426a/426b), a single version of handle 436 can be manufactured that can use thumb wheel 440 (and/or a take-up spool) to take up whatever length of pull wire 28 needs to be retracted in order to achieve deployment of the stent.

The materials that can be used for the various components of system 10 (and/or other systems disclosed herein) may include those commonly associated with medical devices. For simplicity purposes, the following discussion makes reference to inner member 12, sheath 14, and membrane 16. However, this is not intended to limit the invention as the discussion may be applied to other similar members and/or components of members or systems disclosed herein.

Inner member 12, sheath 14, and membrane 16, and/or other components of system 10 may be made from a metal, metal alloy, polymer (some examples of which are disclosed below), a metal-polymer composite, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of inner member 12, sheath 14, and membrane 16 may also be doped with, made of, or otherwise include a radiopaque material including those listed herein or other suitable radiopaque materials.

In some embodiments, a degree of MRI compatibility is imparted into system 10. For example, to enhance compatibility with Magnetic Resonance Imaging (MRI) machines, it may be desirable to make inner member 12, sheath 14, and membrane 16, in a manner that would impart a degree of MRI compatibility. For example, inner member 12, sheath 14, and membrane 16, or portions thereof, may be made of a material that does not substantially distort the image and create substantial artifacts (artifacts are gaps in the image). Certain ferromagnetic materials, for example, may not be suitable because they may create artifacts in an MRI image Inner member 12, sheath 14, and membrane 16, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers that may be used to form inner member 12, sheath 14, and membrane 16, and/or other components of system 10 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6% LCP.

In some embodiments, the exterior surface of the system 10 may include a coating, for example a lubricious, a hydrophilic, a protective, or other type of coating. Hydrophobic coatings such as fluoropolymers provide a dry lubricity which improves device handling and exchanges. Lubricious coatings improve steerability and improve lesion crossing capability. Suitable lubricious polymers may include silicone and the like, polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, the entire disclosures of which are incorporated herein by reference.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A stent delivery system, comprising:
an inner member;
a sheath disposed about the inner member;
wherein the sheath includes a compressible coil;
wherein the compressible coil is capable of shifting between a first configuration and a second configuration;
wherein the sheath has a first length when the compressible coil is in the first configuration and a second length shorter than the first length when the compressible coil is in the second configuration;
a stent disposed between the inner member and the sheath;
a membrane extending between the inner member and the sheath;
wherein the membrane is configured to be disposed on the stent;
an outer member disposed over the sheath;
wherein the inner member has a stent receiving region for receiving the stent;
wherein a distal end of the outer member is disposed proximally of the stent receiving region; and
wherein a distal end of the compressible coil is disposed at a common axial position with the distal end of the outer member.

2. The stent delivery system of claim 1, wherein the coil extends along substantially the entire length of the sheath.

3. The stent delivery system of claim 1, wherein sheath includes a polymer.

4. The stent delivery system of claim 3, wherein the polymer is configured to deflect radially inward when the coil is compressed.

5. The stent delivery system of claim 1, wherein the coil includes a first coil region having a first pitch and a second coil region having a second pitch different from the first pitch.

6. The stent delivery system of claim 1, wherein the coil has a variable pitch along the length of the sheath.

7. The stent delivery system of claim 1, wherein the coil includes a first coil region having a closed pitch and a second coil region having an open pitch.

8. The stent delivery system of claim 1, wherein the sheath includes a plurality of compressible coils.

9. The stent delivery system of claim 1, further comprising a handle disposed at a proximal end of the stent delivery system, the handle including a pressurization port for infusing fluid into a pressurization lumen defined between the inner member and the sheath.

10. The stent delivery system of claim 1, wherein the sheath includes a pull wire extending proximally therefrom and wherein proximal retraction of the pull wire results in compression of the compressible coil.

\* \* \* \* \*